United States Patent [19]

Song et al.

[11] Patent Number: 5,418,222
[45] Date of Patent: May 23, 1995

[54] MULTI-LAYERED COLLAGEN FILM COMPOSITIONS FOR DELIVERY OF PROTEINS AND METHODS OF USING SAME

[75] Inventors: Suk-Zu Song, Moorpark; Andrew Morawiecki, Camarillo; Glenn F. Pierce, Thousand Oaks; Colin G. Pitt, Westlake Village, all of Calif.

[73] Assignee: Amgen Inc., Thousand Oaks, Calif.

[21] Appl. No.: 267,647

[22] Filed: Jun. 28, 1994

Related U.S. Application Data

[63] Continuation of Ser. No. 716,862, Jun. 18, 1991, abandoned, which is a continuation-in-part of Ser. No. 715,165, Jun. 14, 1991, abandoned.

[51] Int. Cl.⁶ .............. A61K 37/02; A61K 47/42; A61L 15/22; A61L 15/32
[52] U.S. Cl. ....................... 514/21; 514/801; 514/964; 424/443; 424/444; 424/445; 424/447; 424/449; 424/425; 602/50
[58] Field of Search .............. 530/356; 514/21, 801, 514/964; 424/443, 444, 445, 447, 449, 425; 602/50

[56] References Cited

U.S. PATENT DOCUMENTS

| | | | |
|---|---|---|---|
| 4,060,081 | 11/1977 | Yannas et al. | 602/49 |
| 4,148,664 | 4/1979 | Cruz | 106/161 |
| 4,606,337 | 8/1986 | Zimmerman et al. | 602/48 |
| 4,759,354 | 7/1988 | Quarfoot | 602/50 |
| 4,808,402 | 2/1989 | Leibovich et al. | 424/78.06 |
| 4,837,285 | 6/1989 | Berg et al. | 530/356 |
| 4,841,962 | 6/1989 | Berg et al. | 602/50 |
| 4,865,846 | 9/1989 | Kaufman | 424/428 |
| 4,909,244 | 3/1990 | Quarfoot et al. | 602/48 |
| 4,950,483 | 8/1990 | Ksander et al. | 424/422 |
| 5,030,215 | 9/1991 | Morse | 604/410 |
| 5,104,660 | 4/1992 | Chvapil et al. | 424/445 |
| 5,196,185 | 3/1993 | Silver et al. | 424/45 |

FOREIGN PATENT DOCUMENTS

| | | |
|---|---|---|
| 0256785 | 1/1963 | Australia . |
| 227955 | 7/1987 | European Pat. Off. . |
| WO85/04413 | 10/1985 | WIPO . |

*Primary Examiner*—Michael G. Wityshyn
*Assistant Examiner*—Nancy J. Gromet-Degen
*Attorney, Agent, or Firm*—Daniel M. Chambers; Daniel R. Curry

[57] ABSTRACT

The present invention relates to single and multiple layer collagen films that are useful for improved sustained release delivery of pharmaceuticals.

45 Claims, 9 Drawing Sheets

MULTI-LAYERED COLLAGEN FILM COMPOSITIONS FOR DELIVERY OF PROTEINS AND METHODS OF USING SAME

This application is a continuation of U.S. patent application Ser. No. 07/716,862, filed Jun. 18, 1991, now abandoned, which is a continuation-in-part of U.S. patent application Ser. No. 07/715,165, filed Jun. 14, 1991, now abandoned.

BACKGROUND OF THE INVENTION

The present invention relates to single and multiple layer collagen films that are useful for improved sustained release delivery of pharmaceuticals.

Various membranes containing collagen have been used in the prior art. Abbenhaus et al., Surg. Forum 16:477-478 (1965) disclosed collagen films of 2 to 3 millimeter thickness that were produced by heating and dehydrating collagen extracted from cow hides. Chu disclosed non-chemically crosslinked collagen implants produced by compression, which are useful for sustained drug delivery [European Patent Application 187014, published Jul. 9, 1986; U.S. Pat. No. 4,600,533, issued Jul. 15, 1986; U.S. Pat. No. 4,655,980, issued Apr. 7, 1987; U.S. Pat. No. 4,689,399, issued Aug. 25, 1987; and PCT Patent Application WO 90/00060, published Jun. 28, 1989]. Cioca [U.S. Pat. No. 4,412,947, issued Nov. 1, 1983], disclosed an essentially pure collagen sheet made by freeze drying a suspension of collagen in an organic acid. Kuroyanagai et al. [European Patent Application 167828, published Jan. 15, 1984; U.S. Pat. No. 4,642,118, issued Feb. 10, 1987], disclosed an artificial skin composed of two layers: collagen and a poly-alpha-amino acid. Berg et al. [U.S. Pat. No. 4,841,962, issued Jun. 27, 1989], disclosed a wound dressing composed of three layers: an adhesive, a cross-linked collagen matrix, and a multilayer polymer film. Holman, U.S. Pat. No. 4,950,699, issued Aug. 21, 1990, disclosed a wound dressing consisting of less than 10 percent collagen mixed with an acrylic adhesive. Cioca et al., British Patent 1,347,582, disclosed a collagenic wound dressing consisting of a freeze dried polydisperse collagen mixture. Steffan et al., European Patent 069260, published Jan. 12, 1983, disclosed a collagen insert consisting of high purity native collagen. Zimmerman et al. [U.S. Pat. No. 4,453,939, issued Jun. 12, 1984], disclosed a wound healing composition containing collagen coated with fibrinogen, factor XIII fibrinogen, and/or thrombin. Leibovich et al. [U.S. Pat. No. 4,808,402, issued February 1989], disclosed a composition for treating wounds comprising collagen, bioerodible polymer, and tumor necrosis factor. Yannas and Burke [J. Biomed. Mat. Res. 14:68–81 (1980)], have reviewed the design of artificial skin, some examples of which contain collagen. Chvapil et al., Int. Rev. Connect. Tissue Res. 6:1–61 (1973), particularly at pages 51 to 52; and Pachence et al., Med. Device and Diag. Ind., 9:49–55 (1987), disclose various uses of collagen, including its use as a drug delivery vehicle.

In addition, collagen has been used as a component in pharmaceutical sponges [Artandi, U.S. Pat. No. 3,157,524, issued Nov. 17, 1964; Berg et al., U.S. Pat. No. 4,320,201, issued Mar. 16, 1982; Berg et al., U.S. Pat. No. 4,837,285, issued Jun. 6, 1989; Doillon et al., Scanning Electron Microscopy III:1313-1320 (1984); Doillon and Silver, Biomaterials 7:3-8 (1986); Doillon et al., Biomaterials 8:195-200 (1987); Oluwasanmi et al., J. Trauma 16:348-353 (1976); Collins et al., Surg. Forum 27:551-553 (1976)] and salves [PCT Patent Application WO 86/03122, published Jun. 5, 1986]. Collagen has also been used for wound healing in conjunction with electrical currents [U.S. Pat. No. 4,937,323, issued Jun. 26, 1990].

Although some previously utilized collagen containing films have demonstrated sustained release characteristics, they are by no means optimal for steady, even, and continuous release of therapeutic agents over an extended period of time. The present invention provides a much desired improvement in wound dressings by providing for such a steady, even, and continuous release of therapeutic agents over an extended period of time.

SUMMARY OF THE INVENTION

The present invention relates to a collagen film comprising one or two rate controlling layers and one or more drug reservoirs layers, said layers contacting each other to form a stack such that the rate controlling layer is situated at an end of the stack, with the proviso that said rate controlling layer contacts only one other layer, said other layer being a drug reservoir layer. Preferably, one or both rate controlling layers is void of any active ingredient and more preferably there are from 1 to 5 drug reservoir layers. Preferably, the drug reservoir layer and/or the rate controlling layers have a thickness of from about 0.01 to about 1 mm, more preferably from about 0.05 to about 0.5 mm, and most preferably from about 0.2 to about 0.2 mm.

Another aspect of the present invention is a collagen film comprising one or more drug reservoir layers, said layers contacting each other to form a stack of said drug reservoir layers.

Preferably, the first rate controlling and/or drug reservoir layer further comprise a plasticizer and/or a stabilizing agent and/or a drying enhancer and/or a buffer. Active ingredients are preferably selected from the group consisting of PDGF, EGF, FGF, PDEGF, PD-ECGF, KGF, IGF-1, IGF-2, TNF, BDNF, CNTF, and NT-3. More preferably, the active ingredient is either PDGF or PD-ECGF.

Another aspect of the present invention is a collagen film further comprising a second rate controlling layer, such that said second rate controlling layer is situated at an end of the stack opposite to the end occupied by the first rate controlling layer.

Another aspect of the present invention is a method of enhancing wound healing of an epidermal wound comprising administration of a wound healing effective amount of an active ingredient via a collagen film of the present invention.

Another aspect of the present invention is a method of enhancing wound healing of an internal wound comprising administration of a wound healing effective amount of an active ingredient via a collagen film having two rate controlling layers at opposite ends of a stack.

DETAILED DESCRIPTION OF THE INVENTION

Figure 1:
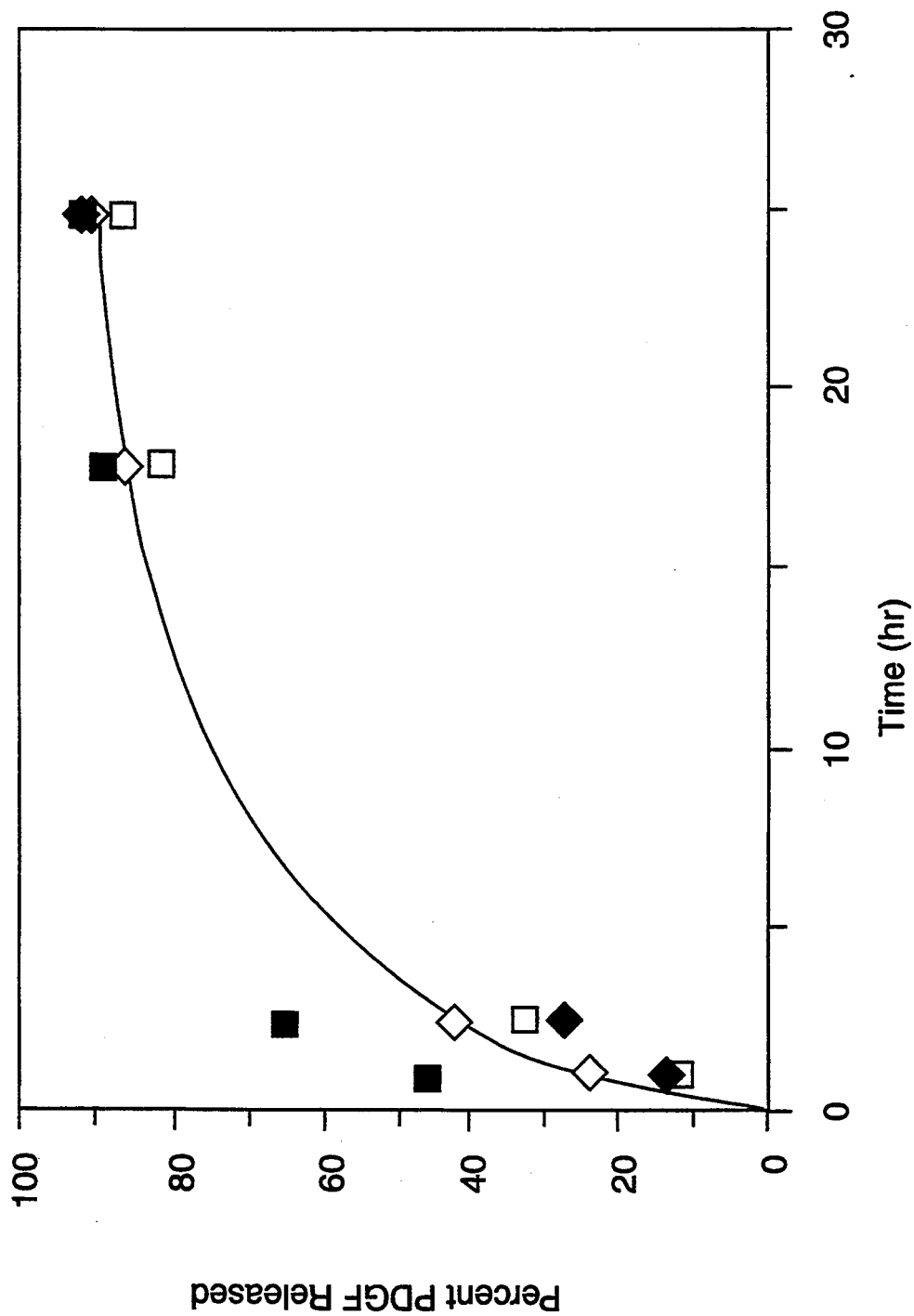
FIG. 1 shows the release rate profile of PDGF from a single layer collagen film (thickness 0.1 mm) made from insoluble collagen fibrils as described in Example 1B.

The present invention relates to a collagen film comprising one or two rate controlling layers and one or more drug reservoir layers, said layers contacting each other in a stacked conformation such that a rate controlling layer is situated at one or both ends of the stack, with the proviso that said rate controlling layer contacts only one other layer, said other layer being a drug reservoir layer. Preferably, there is only one rate controlling layer, which is situated at one end of the stack.

Rate controlling layers can be produced from a solution of soluble collagen. Soluble collagen is collagen that has an average molecular weight of less than 400,000, preferably having a molecular weight of about 300,000. A particularly suitable soluble collagen is Semex S (Semex Medical Co., Malvern, Pa.). This particular soluble collagen is also advantageous because it is the atelopeptide form of the collagen. Atelopeptide collagen is collagen that is free of telopeptide, which is a peptide located at one end of purified collagen often associated with immunogenicity. A solution of the telopeptide form of collagen can be converted to the atelopeptide form of collagen via hydrolysis using organic acid. Another preferred characteristic of the soluble collagen is that it possesses a minimal amount of crosslinking, i.e., 0.5% or less.

The soluble collagen can be dissolved in a suitable solvent such as water to produce a solution that contains from about 0.5 to about 10% of collagen by weight, preferably from about 1 to about 5% by weight, and more preferably about 2% by weight.

Rate controlling layers can also be produced from a dispersion of collagen fibrils in suspension. Collagen fibrils, which are commercially available (e.g., Vitaphore Co., Menlo Park, Calif.), can be dispersed into a suitable solvent such as water to produce a suspension that contains from about 0.1 to about 10% of collagen by weight, preferably from about 1 to about 2% of collagen by weight. To aid in the dispersion of the collagen fibrils into the suspension, a suitable dilute acid can be present in the solvent. A particularly suitable acid is acetic acid at a concentration of about 5%.

A solution of soluble collagen or a dispersion of collagen fibrils in suspension is prepared as a film using a solvent casting method. Typically, the collagen solution is poured into a mold and allowed to dry. Preferably, the mold has the property of being nonstick so that the dried collagen film will not adhere to the surface of the mold. A particularly suitable mold surface is Teflon™. Suitable conditions include allowing the poured solution to dry at a suitable temperature for a suitable period of time. Generally, the amount of drying time necessary is shorter as the drying temperature is raised. Specifically, a suitable temperature is from about 15° C. to 35° C., preferably about room temperature, and a suitable drying time is sufficient time so that the marginal loss of solvent content is essentially zero (e.g., drying time of about an hour to about 10 days, preferably about one to about five days).

Since the most important factors affecting the rate of release of active ingredients is the thickness of the film and the presence/amount of plasticizers in the rate controlling layer, it is critical to achieve a suitable thickness of the dried film. Particularly suitable thicknesses for such rate controlling layers are from about 0.01 to about 1 mm, preferably from about 0.05 to about 0.5 mm, and most preferably from about 0.1 to about 0.2 mm.

To optimize desirable characteristics of a preferred collagen film, various additives may be optionally included in the collagen solution and film. Such desirable characteristics include flexibility, stability, accelerated drying time and a pH compatible with the active ingredient to be utilized.

To improve flexibility, a suitable plasticizer can be used. Suitable plasticizers include polyethylene glycol and glycerol, preferably glycerol. Such plasticizers can be present in an amount from zero to about 100% of the weight of collagen present, preferably from about 10 to about 30% of the weight of collagen present, and most preferably about 20% of the weight of collagen present.

To improve the stability of the active ingredient, a suitable stabilizing agent can be used in the film. Suitable stabilizing agents include most sugars, preferably mannitol, lactose, and glucose, more preferably mannitol. Such stabilizing agents can be present in an amount from zero to about 5% of the weight of collagen present, preferably about 1% of the weight of collagen present.

To accelerate drying time for the films, a drying enhancer can be used. Suitable drying enhancers include alcohols, preferably ethanol, methanol and isopropyl alcohol, more preferably ethanol. Such drying enhancers can be present in an amount from zero to about 50% of the weight of the total solution or suspension, preferably from about 10 to about 30% of the weight of the total solution or suspension, more preferably about 20% of the weight of the total solution or suspension.

To produce a pH that is compatible with a particular active ingredient being used, a suitable buffer can be used in the film. Suitable buffers include most of the commmonly known and utilized biological buffers, preferably acetate, phosphate and citrate, more preferably acetate and phosphate. Such buffers can be present in an amount of from about 0.01% to about 2% of the weight of the collagen. A compatible pH is one that maintains the stability of an active ingredient, optimizes its therapeutic effect or protects against its degradation. A suitable pH is generally from about 3 to about 8, preferably about 5 to about 8, and most preferably about neutral pH of from about 7.0 to about 7.5.

Although the active ingredient is not usually present in the rate controlling layer, the present invention does contemplate such an embodiment. Active ingredient can, therefore, be formulated into the rate controlling layer. However, the presence of any active ingredient in the rate controlling layer is preferably at a concentration that is lower than the concentration of active ingredient in any drug reservoir layer.

Drug reservoir layers are produced in the same manner as the rate controlling layer with additional active ingredient if there is active ingredient in the rate controlling layer or with the presence of active ingredient if there is no active ingredient in the rate controlling layer. Preferred active ingredients are those biological agents which enhance wound healing or regeneration of nerve tissue, particularly recombinant proteins. Such preferred active ingredients include platelet derived growth factor (PDGF), epidermal growth factor (EGF), fibroblast growth factor (FGF), platelet derived epidermal growth factor (PDEGF), platelet derived endothelial cell growth factor (PD-ECGF) keratinocyte growth factor (KGF), insulin-like growth factors 1 and 2 (IGF-1 and IGF-2), tumor necrosis factor (TNF), brain derived neurotrophin factor (BDNF), ciliary neurotrophic factor (CNTF) and neurotrophin-3 (NT-3). A preferred active ingredient is PDGF or PD-ECGF, most preferably PDGF. Such active ingredients are present in an amount sufficient to enhance healing of a wound, i.e., a wound healing effective amount. The actual amount of the active ingredient will be determined by the attending clinician and will depend on various factors such as the severity of the wound, the condition of the patient, the age of the patient and any collateral injuries or medical ailments possessed by the patient. Generally, the amount of active ingredient will be in the range of about 1 $\mu$g/cm$^2$ to 5 mg/cm$^2$.

Particularly suitable thicknesses for drug reservoir layers are from about 0.01 to about 1 mm, preferably from about 0.05 to about 0.5 mm, and most preferably from about 0.1 to about 0.2 mm.

The various layers contact each other by any number of methods. One such method is to place layers adjacent to each other and apply pressure to the outer sides of the layers to force the layers together. Another method is to coat the surface of each of the layers to be contacted with a solvent, such as water, before placing the layers together. In this way, a thin portion of each surface will become soluble thereby producing adhesion upon contact. Another method is to use a known adhesive on one or more of the contacting surfaces. Preferably, the adhesive is one that will not interfere with the release of the active ingredient from a layer. The preferred method of contacting the layers is with the application of equal pressure on each of the layers to be contacted.

The number of drug reservoir layers is determined by the desired release characteristics. Generally, more layers produce a more steady and more sustained release of the active ingredient. Preferably, the number of drug reservoir layers is from 1 to 10, more preferably from 1 to 5 and most preferably from 1 to 3. The concentration of active ingredient in different layers can be varied and the thickness of the different layers need not be the same.

The rate controlling layer may be at one or both ends of the stack. A stack of layers with a rate controlling layer at only one end is particularly suited to deliver an active ingredient to an epidermal surface. A stack of layers with a rate controlling layer at both ends is particularly suited to deliver an active ingredient to an internal wound or to a two surfaced wound, such as a surgical incision.

When there is only one rate controlling layer at one end of the stack, the other end of the stack may optionally consist of a backing layer. Such a backing layer can be any of the conventionally known backing layers. Generally, the backing layer comprises polyurethanes.

The collagen films of the present invention are useful as a means of delivering the active ingredient to cells or tissue with which it is in contact. For example, in the treatment of burns or other traumas to the skin, a collagen film with one rate controlling layer and one backing layer can be placed on the wound to deliver a suitable active ingredient to the traumatized area. PDGF is a particularly suitable active ingredient for such uses. Collagen films with rate controlling layers at both ends of the stack can be used to accelerate healing of surgical wounds. When used in such a way, the film can be placed in the surgical incision and stitched into the wound as an interface between the two surgical wound surfaces. Collagen films can also be used to deliver neurotrophic factors. When used in such a manner, the collagen film can be placed in direct contact with or adjacent to the nerve tissue to be treated with the neurotrophic factor.

EXAMPLES

The following examples are intended to exemplify specific embodiments of the present invention without limiting the scope in any way.

Example 1: Preparation of a Single Layer Collagen Film

A. Soluble Collagen

Collagen films containing various growth factors were prepared by the solvent casting method from a solution of soluble collagen. The soluble collagen was purchased from Semex Co. (Frazer, Pa.). This collagen is from bovine origin and it contains 99% type I collagen and 1% type III collagen. The molecular weight of the collagen is 300K dalton and the density is 0.044 gram/cc. The antigenicity of the collagen is minimal since the telopeptide is removed from the collagen.

First, a collagen solution (about 1 to 8%) was prepared by dissolving the soluble collagen in 0–5% acetic acid solution at 18°–70° C. After the addition of the plasticizer glycerol (about 20% of the dry weight of the collagen), ethanol was added to the solution to facilitate the solvent evaporation process. The amount of alcohol was about 20% of the amount of the solution. The solution is then centrifuged to remove the undissolved material.

Figure 6:
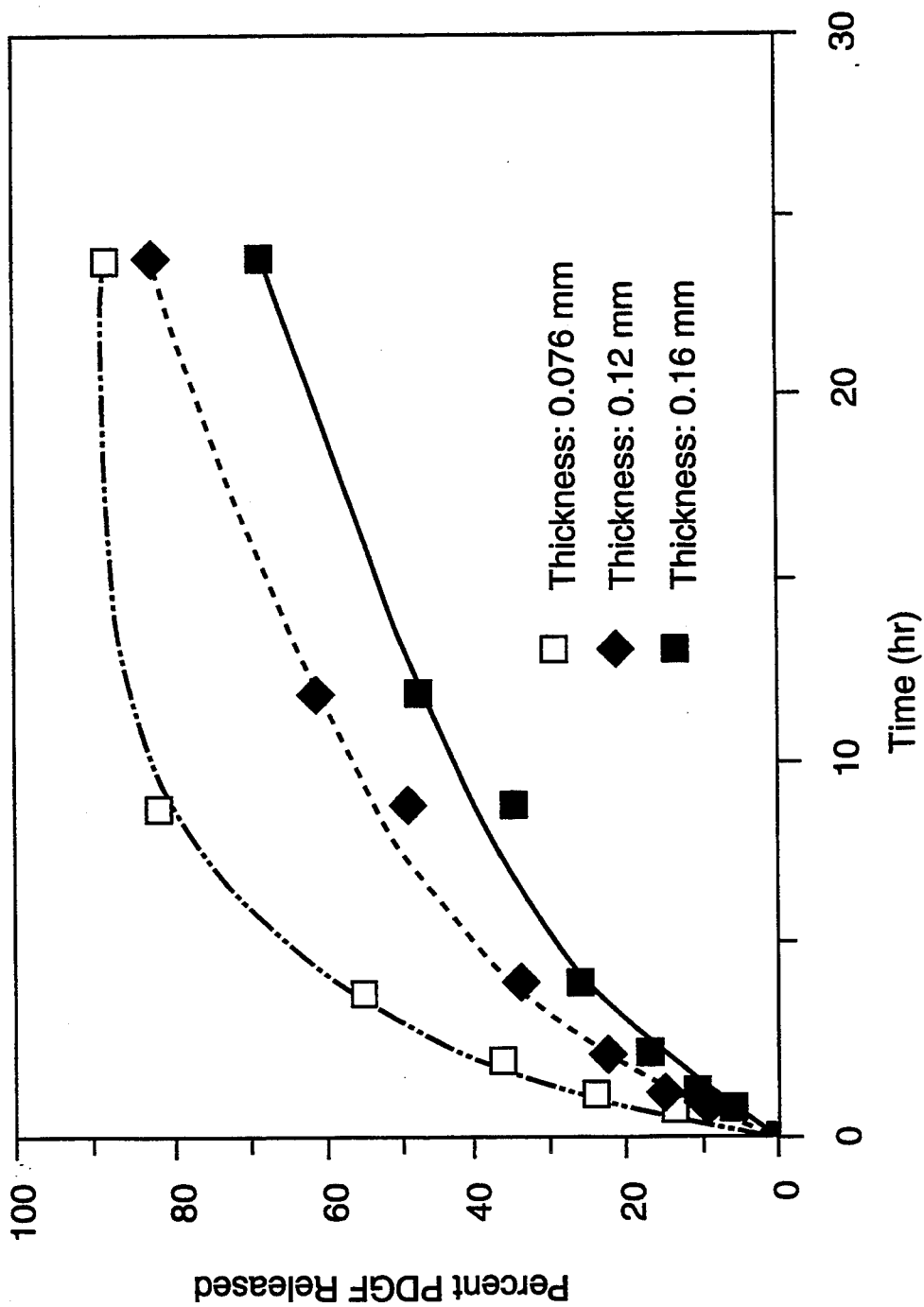
FIG. 6 shows the release rate profile of PDGF from a single layer collagen film (thicknesses 0.01–3.0 mm) made from soluble collagen as described in Example 1A.

A growth factor solution (with or without radioactive material) was added to the solution. The solution was cast on a Teflon ™ surface and dried at room temperature until the weight of the film was constant (for about 1–3 days) to produce collagen films containing various amounts of growth factor. Table I shows the thickness of the films prepared from the different concentrations of the collagen solution. FIG. 6 shows the release profiles of PDGF from the collagen films with the release profiles being obtained by using the methods of Example 4 for various single layer films.

TABLE 1

Thickness of Collagen Films

| Diameter of the Container | Volume of the Collagen Solution | Thickness of the Film |
|---|---|---|
| A. 4% Collagen Solution | | |
| 3.5 cm | 1.5 ml | 1.8 mil |
| | 7.5 ml | 10 mil |
| 5.0 cm | 3.2 ml | 1.8 mil |
| | 3.6 ml | 2 mil |
| | 9.4 ml | 3 mil |
| B. 8% Collagen Solution | | |
| 5.0 cm | 2.25 ml | 2.5 mil |
| | 2.25 ml | 2.8 mil |
| | 2.25 ml | 2.7 mil |

B. Collagen Fibril Suspension

Wafers made of insoluble collagen fibril were prepared and the release rate of PDGF was measured. 2 grams of insoluble fibril collagen (Vitaphore Co., Menlo Park, Calif.) was dispersed in about 110 ml of 5% acetic acid solution containing 0.2 ml glycerol. To the resulting solution, about 10 ml of PDGF solution (782 μg/ml) containing a trace amount of $^{125}$I-PDGF was added. Five ml of alcohol was added to expedite the solvent evaporation process. Three films were cast from the mixture to obtain three different film thicknesses. Several wafers were cut from each film. The average thickness of the films was 0.10, 0.36, and 0.48 mm for Film-A, Film-B, and Film-C, respectively. The release rate of PDGF from each wafer was measured with a Franz diffusion cell (Crown Glass Co., Sommerville, N.J.), which is commonly used for the determination of drug release rate from a transdermal patch. By using a Franz diffusion cell, a reasonable perfect sink condition could be obtained. A piece of Durapore membrane (Millipore Co., Bedford, Mass.) (pore size 5 μm) was used to separate the collagen wafer from the receiver solution.

Figure 2:
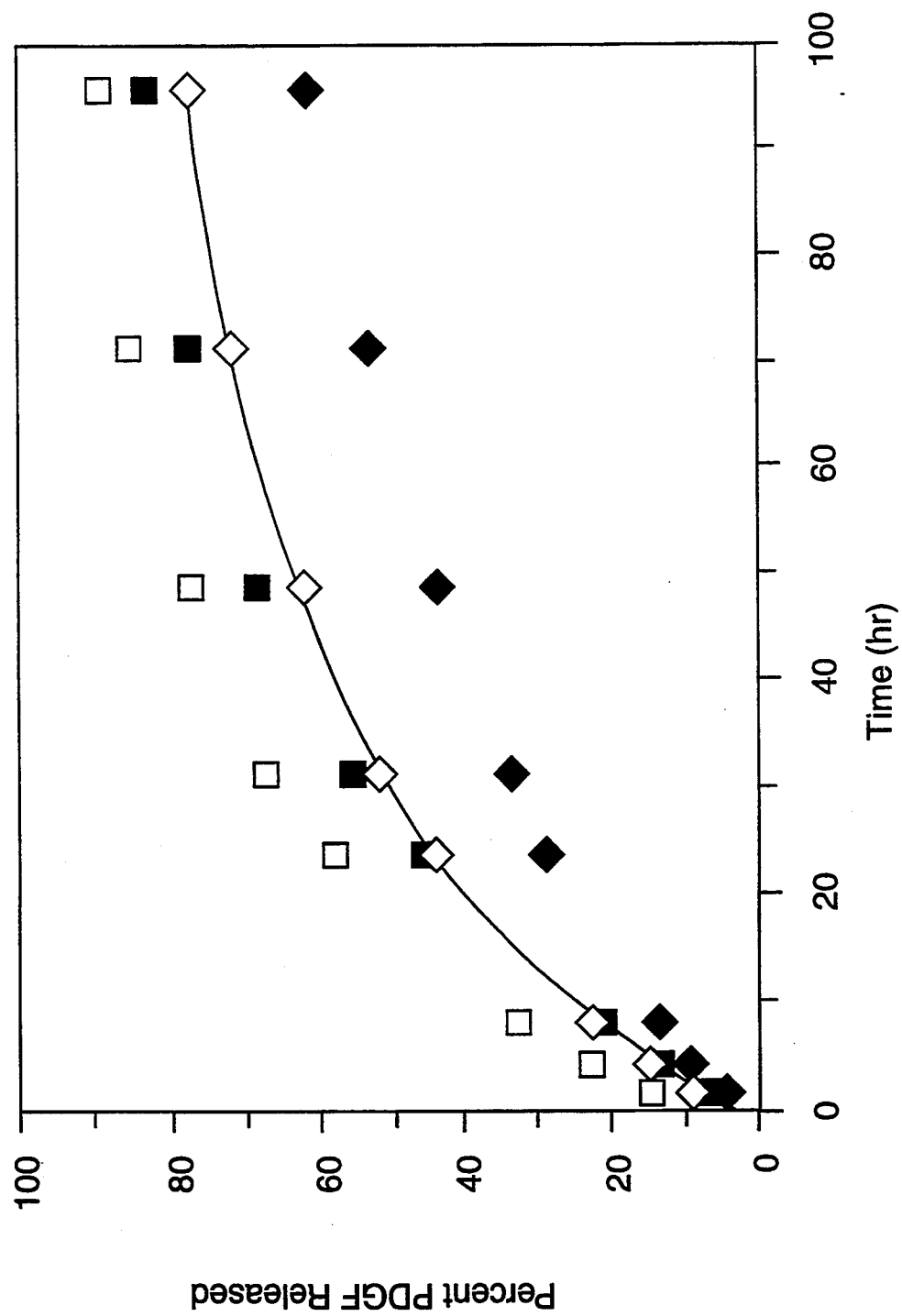
FIG. 2 shows the release rate profile of PDGF from a single layer collagen film (thickness 0.36 mm) made from insoluble collagen fibrils as described in Example 1B.
Figure 3:
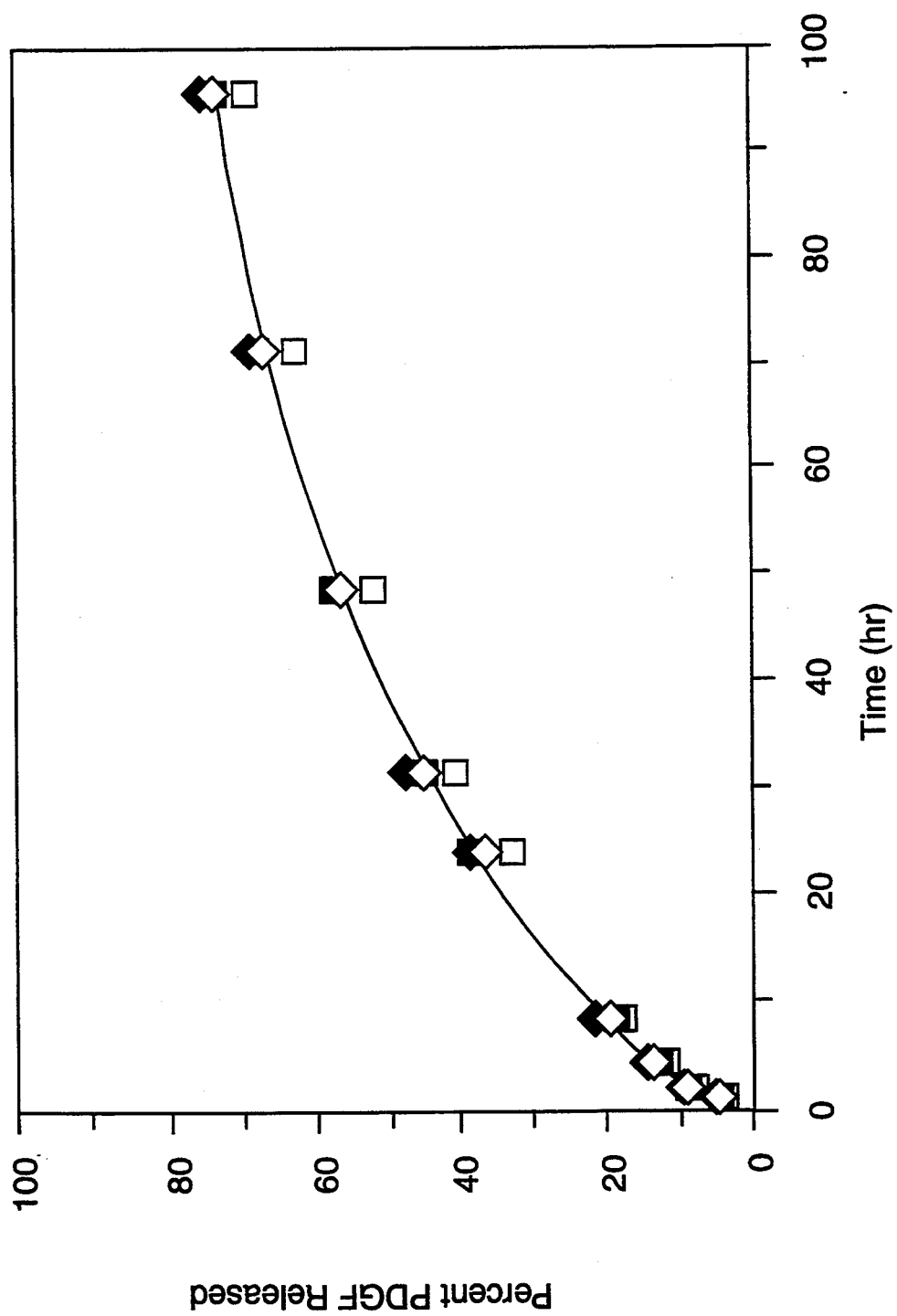
FIG. 3 shows the release rate profile of PDGF from a single layer collagen film (thickness 0.48 mm) made from insoluble collagen fibrils as described in Example 1B.

FIG. 1 shows the release profile of PDGF from wafers cut from Film-A (thickness 0.1 mm). Most of the PDGF was released in 24 hours. FIG. 2 shows the release profile of PDGF from wafers cut from Film-B (thickness 0.36 mm). About 77% of PDGF was released in 96 hours. FIG. 3 shows the release profile of PDGF from wafers cut from Film-C (thickness 0.48 mm). About 73% of PDGF was released. Data shown in FIGS. 1, 2, and 3 indicate that the duration of PDGF release may be controlled from one day to more than one week.

Example 2: Preparation of Double Layer Collagen Film

Figure 4:
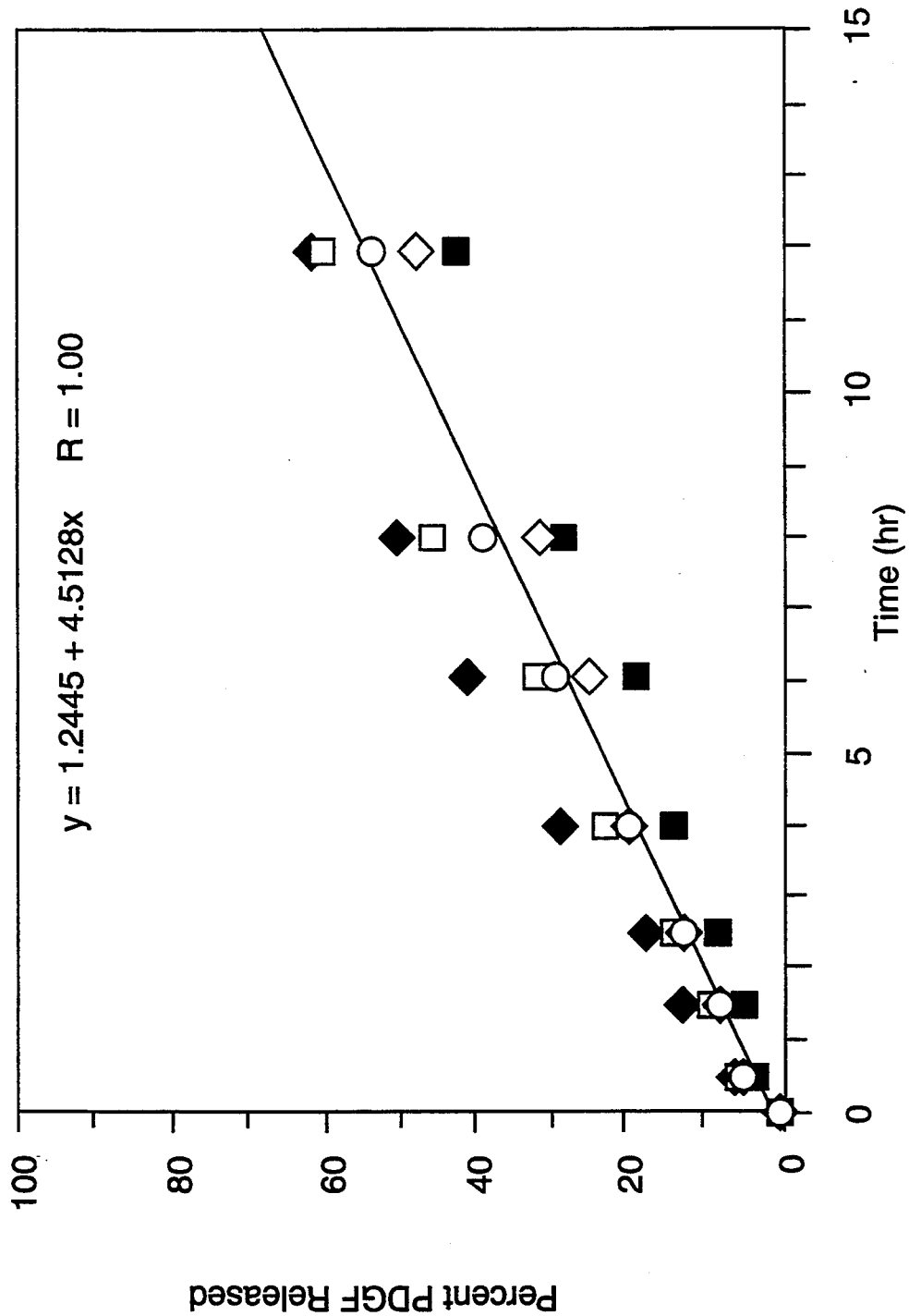
FIG. 4 shows the release rate profile of PDGF from a double layer collagen film (thickness 0.01–3.0 mm) made from soluble collagen as described in Example 2.

Double layer films of collagens were used to produce wound dressings which can deliver growth factors at a nearly constant rate to the wound sites for long periods of time (12 hours or longer). In one experiment, one collagen layer (membrane A) was prepared by a solvent casting method from an aqueous solution containing soluble collagen (4% collagen in 10 mM acetate buffer (pH 4) in 0.85% NaCl solution), glycerol (20% w/w of collagen), and ethanol (20% of the solution). The second film (membrane B) had almost the same thickness (0.01–3 mm) and the same composition as the first film except it contained PDGF (20 μg/cm² film). The two films were combined into one by attaching them together by evenly applying pressure. An in vitro release rate study conducted according to Example 4 showed that the growth factor was released at a constant rate for more than 12 hours (FIG. 4).

Example 3: Preparation of a Multiple Layer Collagen Film

Figure 5:
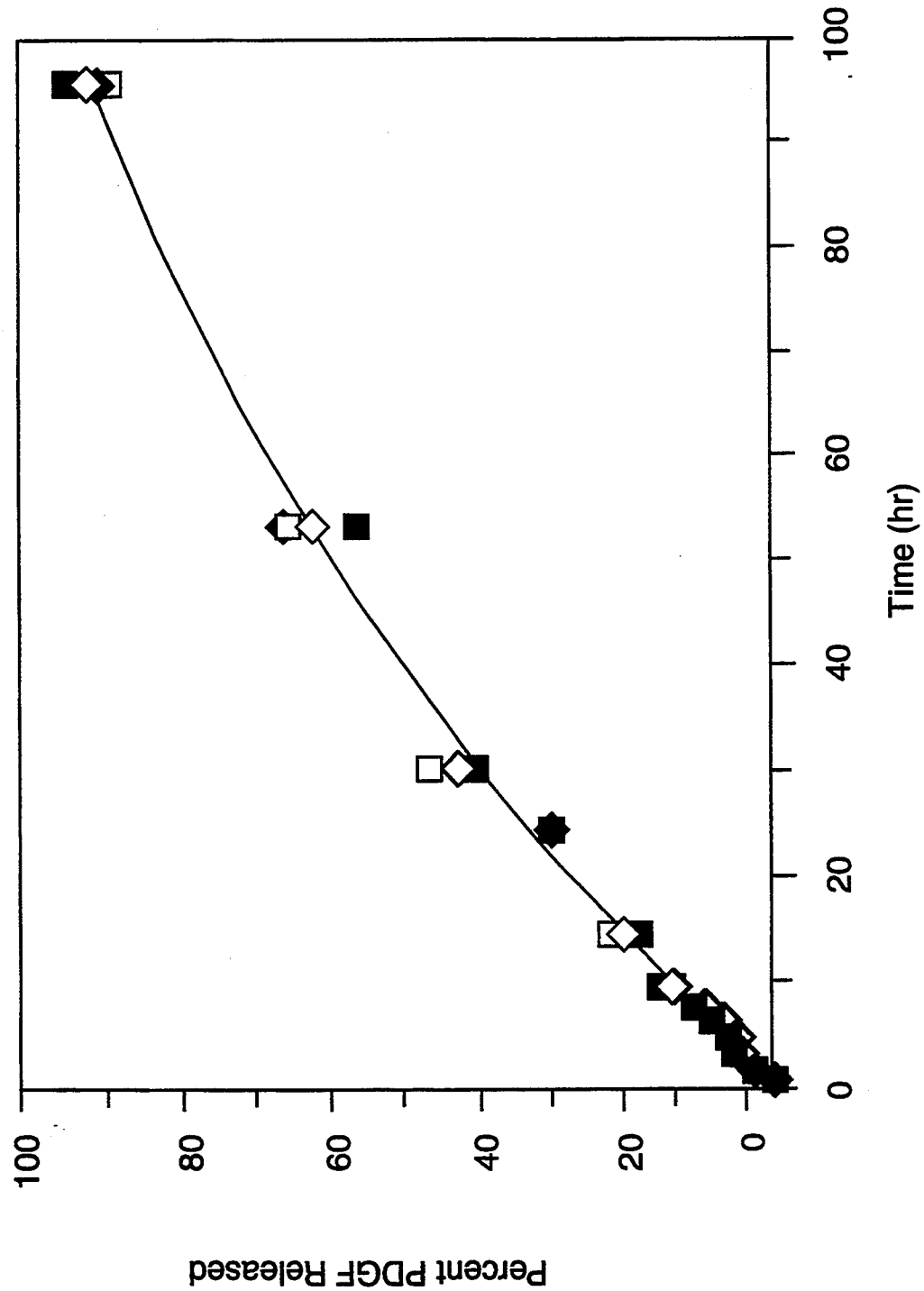
FIG. 5 shows the release rate profile of PDGF from a four layer collagen film (thicknesses 0.01–3.0 mm) made from soluble collagen as described in Example 3.

A three layer film or a four layer film was prepared to produce a long term delivery device of growth factors. In one example a four layer film was prepared by the following method. Four different castings were performed as in Example 1A and then the films were combined into one by attaching them together by evenly applying pressure. The thickness of each layer was similar (0.01–3 mm) however, different thickness layers could be used. The first collagen layer which will contact the skin did not contain PDGF. The concentrations of PDGF were 0.07%, 0.15% and 0.30% for the second the third and the fourth layers respectively. Subsequent release studies showed that a nearly constant release rate of the growth factor was maintained up to 100 hours (FIG. 5). At that time, almost 90% of the growth factor was released.

Example 4: Measurement of Release Kinetics

Figure 7:
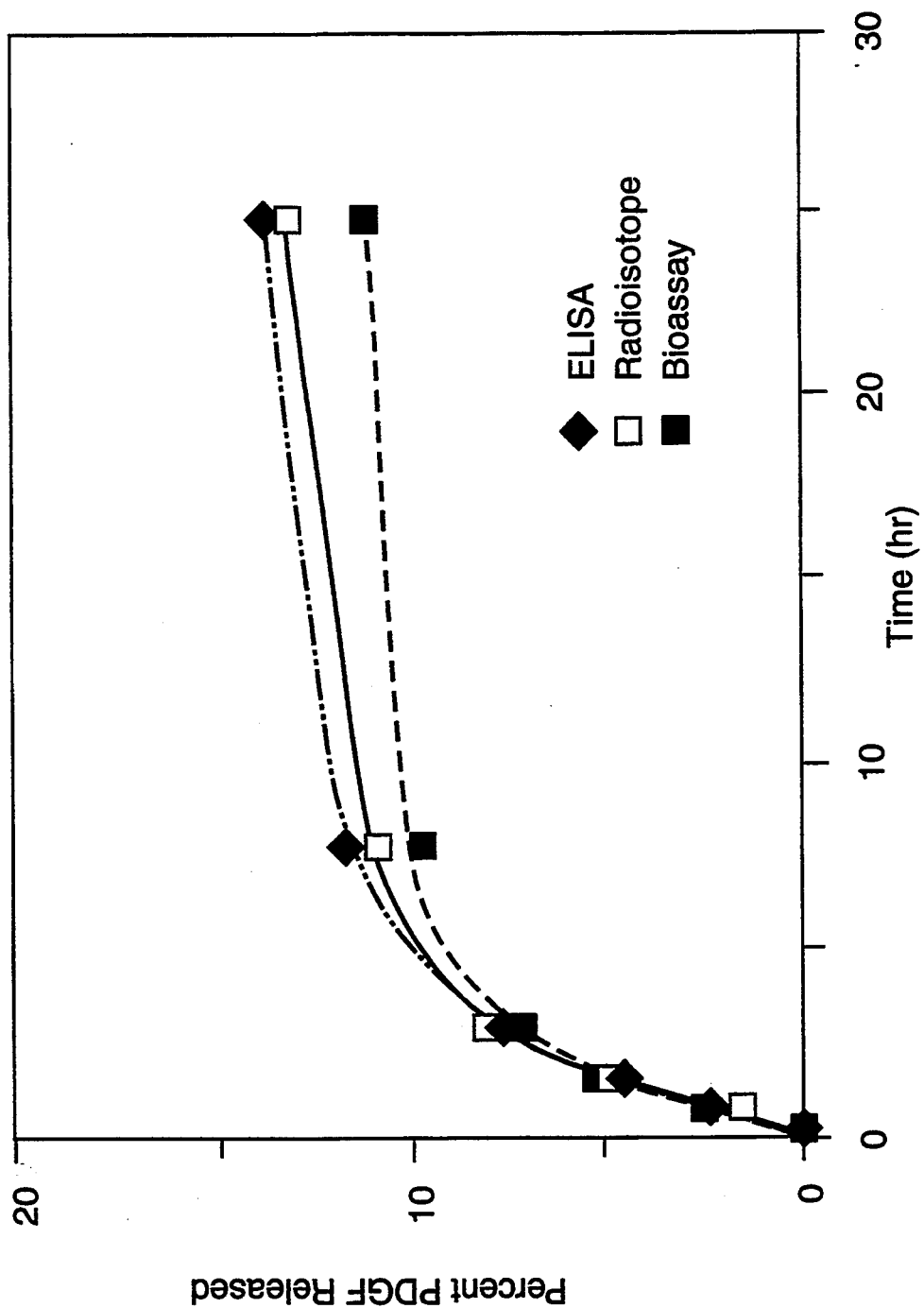
FIG. 7 shows the measurement of protein concentration in samples taken from Costar Transwell Cells by three different methods: ELISA (closed circles); 125I labelled PDGF (open squares); and $^3$H-Thymidine uptake assay (closed squares).

The measurement of release rates of active ingredients from collagen films was conducted using Coster Transwell Cells ("Cell") (Costar Co., Cambridge, Mass.) as follows. Collagen films were produced as described in Examples 1, 2 and 3, and wafers (1.6 cm diameter) were cut from the films. Each wafer was transferred to a Coster Transwell Cell and placed on top of the polycarbonate membrane. 2.5 ml of the receiver solution (water and 1% bovine serum albumin, or water and 0.25% human serum albumin) was added to the Cell holder. The Cells were set on the solution and the release study was initiated. At specified times, 20 μl of the receiver solution was pipetted out and the same amount of fresh solution was replaced in the receiver solution. The sampling procedure was repeated to get another 20 μl sample. The radioactivity of the sample was measured with a gamma counter (Beckman Instruments, Co., Irvine, Calif.). The concentration of protein in the receiver solution at any given time was calculated based on the radioactivity and was confirmed using other methods such as ELISA and $^3$H-thymidine uptake bioassays. Results obtained using this assay are shown in Examples 1, 2, and 3 for films of various layers and thicknesses (FIG. 1 to 6). FIG. 7 shows the agreement of the various methods of measuring protein concentration.

If films were prepared under the standard condition, and the solvent was removed completely under the same conditions, the diffusion coefficient should be independent of the thickness of the film. In general, the release profile of PDGF from the single layer collagen film can be described by the following equation $$F = 2.26 \times (D^{\frac{1}{2}}/L) T^{\frac{1}{2}}$$

wherein:
F = the fraction of the drug released at time T;
D = the diffusion coefficient of PDGF in the swollen film; and
L = the thickness of the swollen film.

The equation shows that the plot of F versus square root of time should be linear. A plot of F versus square root of time showed a linear relationship between the amount of PDGF released and the square root of time.

The diffusion coefficient (D) can be calculated from the slope of the plot and the thickness of the dry collagen film using the above equation. Such a calculation with film thickness of 0.05 mm gave a diffusion coefficient of $3 \times 10^{-9}$ cm$^2$/sec. This value was much smaller than the diffusion coefficient of PDGF in Geliperm membrane. Since the measurement of the swollen collagen film is difficult to measure accurately, the apparent diffusion coefficient (Da) has been defined as:

$$Da = D(Lo/L)^2$$

wherein D and L are defined as above and Lo is the thickness of the dry film. The apparent diffusion coefficient (Da) can be obtained from the slope of the plot of F versus square root of time using the equation $$F = 2.26 \times (Da^{\frac{1}{2}}/Lo)T^{\frac{1}{2}}$$

A comparative study of release rates for PDGF is also shown in FIG. 6.

Using this rate release measurement technique, the effect of film thickness on the release rate of PDGF was investigated. If the films were prepared under the standard condition, and the solvent was removed completely under the same conditions, the diffusion coefficient should be independent of the thickness of the film. The third equation above predicts that the slope of the plot of F versus T$^{\frac{1}{2}}$ should be inversely proportional to the thickness of the film. To test the limitations of the film casting technique, four groups of films were prepared from the same collagen solution under the same evaporation conditions. Each film from one group had a similar thickness (Group A: 0.076 mm, Group B: 0.12 mm, Group C: 0.16 mm, and Group D: 0.29 mm). As expected, the release rate of the growth factor decreased with the thickening of the film. The apparent diffusion coefficients (Da) of PDGF in the collagen films calculated from the data were 2.5, 2.4, 2.5 and 7.6 (all $\times 10^{-10}$ cm$^2$/sec) for films of Groups A, B, C and D, respectively. Ideally, the diffusion coefficient should be the same regardless of the film thickness. The resulting data indicate that the current film casting method is very reliable up to the film thickness of at least 0.16 mm. The higher value of the diffusion coefficient at 0.29 mm is probably caused by the solvent present in the thick films due to incomplete solvent evaporation, indicating that more drying time or elevated temperature is required for the preparation of thick films.

To further study the effect of the initial PDGF concentration on the release profile, seven films were prepared. Each film had a similar thickness (about 0.05 mm) but had a different concentration of PDGF. The release profiles for all seven films were very similar and Table 2 shows the apparent diffusion constants calculated for each of the seven films.

TABLE 2

| | Concentration Effect of PDGF | |
|---|---|---|
| Film | Conc. | Da $\times 10^{10}$ (cm$^2$/sec) |
| A | 1× | 2.09 |
| B | 1× | 2.14 |
| C | 2× | 1.69 |
| D | 5× | 1.54 |
| E | 10× | 1.36 |
| F | 20× | 1.72 |

TABLE 2-continued

| | Concentration Effect of PDGF | |
|---|---|---|
| Film | Conc. | Da $\times 10^{10}$ (cm$^2$/sec) |
| G | 30× | 1.82 |
| Average | — | 1.77 ± 0.28 |

Example 5: Measurment of the Tissue Volume Using the Blood Bundle Model

In 30 Lewis rats (125–150 grams.), the left tibialis posterior and its parent femoral arterio-venous bundle were dissected from the ankle up to the inguinal ligament. The bundles were sandwiched between two collagen disks 1.6 cm in diameter and placed inside a spoon-shaped silastic mold. In 15 rats the disks contained 256 µg of recombinant BB-PDGF (the homodimer form of PDGF, see copending U.S patent application Ser. No. 454,794 and 624,451, filed Dec. 19, 1989 and Dec. 13, 1990, respectively), the remaining 15 rats served as controls, and the disks contained no growth factor. Five control and five experimental animals were sacrificed at days 5, 10, and 15. The contents of the molds were examined grossly, and with a digitizing computer and 3-D reconstruction histomorphometrically to determine the volume of tissue generated. The results are displayed in Table 3.

TABLE 3

| Volume of Tissue Generated (mm$^3$ + standard deviation) | | |
|---|---|---|
| Time (days) | Control | PDGF |
| 5 | 12.6 ± 10.1 | 31.8 ± 15.0 |
| 10 | 15.3 ± 9.8 | 165.9 ± 21.4 |
| 15 | 17.1 ± 10.7 | 209.0 ± 23.5 |

Example 6: Measurement of Wound Healing Using the Rabbit Ear Model

This example measures the influence of growth factors in a collagen film on the rate of healing of surgically created 6 mm diameter dermal ulcers in the rabbit ear. This excisional wound model replicates the healing parameters (i.e., minimal wound contraction, generation of new granulation tissue, reepithelialization) associated with full thickness dermal wounds such as human leg ulcers. The full thickness wound model permitted histologic quantification of both reepithelialization and formation of granulation tissue while excluding wound contracture as a variable. In addition, since cartilage is avascular, and the perichondrium was removed during surgery, new granulation tissue and new epithelium arise solely from the periphery of the wound. PDGF was applied at the time of surgery.

A. Pre-operative Preparation

Young adult New Zealand White rabbits, weighing approximately 3.0 to 3.5 kg each (M & K Rabbitry, Bentonville, Ark.) were anesthesized using Rompum ® (Farbenfabriken, Bayer, West Germany) as a sedative, followed (10 minutes later) by ketamine (60 mg/kg) and xylaine (5 mg/kg), both administered intramuscularly. Each rabbit's weight was measured and recorded. A small cotton or gauze plug was inserted into both ears of each rabbit, after which the inner surface and outer edges of both ears were shaved using an animal clipper (#40 blade). Commercially available Neet ® depilatory cream was then applied to the inner surface of each ear for 10 minutes, after which time it was removed with dry gauze. The inner surface of the ears was wiped with saline-soaked gauze followed by application of a 70% alcohol solution. The dermis of the inner surface on one ear of each rabbit was blanched by infiltration of the ear with a 2% xylocaine solution containing 1:1000 epinephrine (this requires 1.5 to 3.0 mls total volume) using a 30 gauge needle. The infiltrated area was then scrubbed with 3 cycles of betadine followed by the 70% alcohol solution. Where necessary, the ear plugs were replaced with dry plugs at this point.

The rabbits were then transferred to a sterile surgical room. The blanched ear was immobilized on a plexiglass "ear board" (Washington University Medical Center, Division of Technical Services, St. Louis, Mo.) which utilizes two bar clamps, one at the tip and one at the base of the animal's ear, to stabilize the rabbit ear without compromising its blood supply. The animal was draped, and the surgical field (i.e., the inner surface of the blanched ear) sprayed with Betadine and allowed to dry for 3 to 5 minutes.

B. Wounding

Sterile technique was employed thoughout the wounding procedure. Using microsurgical instruments, a 6 mm trephine, and a binocular microscope (10x, Zeiss), the surface of the inner ear of each rabbit was scored gently with a 6 mm biopsy punch, and the biopsy site cleared of all tissue and fibers (including the periosreal membrane) down to the level of bare cartilage, using micro-surgical forceps, tenotomy scissors, a blunt edged 2 mm Lempert periosreal elevator, and sterile cotton-tipped applicators. Perichondrium and overlying tissues were removed by dissection. Biopsies in which the cartilage was completely cut through by the punch were not used for experimental purposes. However, partial thickness scores of the cartilage were considered acceptable. The location of any nicks or natural holes in the cartilage was carefully noted and recorded (for reference on the harvest day). Blood was removed from the biopsy site with sterile, cotton-tipped applicators, with care taken to avoid excess blood in the wound. Each completed biopsy was covered with a small piece of saline-soaked gauze. Four viable 6 mm biopsy ulcers were placed on each wounded ear, two on each side of the midline (as defined by the fold in the ear when it was stabilized upon the board). In any event, no more than 5 total biopsies were placed on each ear. The biopsies were positioned a minimum of 1 cm apart.

Upon completion of one ear, the ear was covered with saline-moistened gauze and then taped shut around the gauze to retain moisture until application of PDGF. The second ear was then blanched, scrubbed, immobilized and wounded in the manner as the first ear. Blood was removed from the biopsy site of each second ear and each completed biopsy covered with a small piece of saline-soaked gauze. Upon completion of the second ear, it was covered with saline-moistened gauze until application of PDGF. Any rabbit that showed evidence of recovery from anesthesia at any time prior to this point in the procedure was reanesthetized with 25 mg/kg ketamine, administered intramuscularly.

C. Application of Active Ingredient to Wounds

Collagen wafers (diameter of 0.5 cm) containing 5.9 µg of PDGF per wafer were prepared from the soluble collagen.

The rabbits were allowed to recover from anesthesia under the observation of the investigator performing the surgery. Upon recovery, a plastic neck collar (Canine Center, St. Louis, Mo.) extending approximately 15 to 25 cm outward was placed around each rabbit's neck to prevent the rabbit from disrupting the wounds or dressings. The rabbits were returned to an isolation cage where they were maintained until harvest. The wounds of any rabbits which had removed their collars, and any wound on which the Tegaderm ® had been disrupted in some way prior to the harvest date, were reevaluated as soon as the problem was noted, and discarded from analysis if the wounds appeared to be damaged.

D. Harvest

At the time of sacrifice, the rabbits were anesthesized in the same manner as described for preoperative preparation. Each rabbit's weight was measured and recorded (each wound being photographed), and a qualitative description of the condition of the wounds was recorded, noting in particular the presence or absence of the Tegaderm ® and of any excess fluid under the dressing. The rabbits were sacrificed with a 50 ml/kg air embolism administered by intracardiac injection. Both ears were then amputated from the body using a #15 surgical blade mounted on a knife handle.

Each biopsy, with approximately 5 mm of surrounding tissue on any side and the Tegaderm ® still intact, was excised from the ear, and the biopsy site measured in order to bisect it accurately at the midline, making reference to notes taken on the day of wounding to avoid bisecting through natural holes or nicks in the cartilage. The biopsy was carefully bisected with a single edge razor blade, using a single downward motion to avoid disrupting the wound orientation. The bisected biopsies were immediately placed in cassettes labeled with the rabbit identification number, and fixed in 10% buffered formalin for routine histologic processing.

E. Quantitative Histological Analysis

In preliminary experiments, the methods of histologic analysis was validated on day zero wounds and wounds were examined at 3, 5, 7, 10 and 14 days, postwounding. At day 3, no reepithelialization had occurred. At days 10 and 14, all of the wounds were fully reepithelialized. Therefore, days 5 and 7 were selected for further analysis.

Carefully oriented 5 mm cross sections through bisected wounds were embedded, sectioned, and stained, using a mixture of Hematoxylin and Eosin. Rough cutting of the section was minimized in order to obtain a cross section through the true wound center. The reepithelialization gap (EG) across the wound, the maximum height (MH) of granulation tissue at the advancing edges of the wound, and the granulation tissue gap (GTG) across the wound, were measured using a calibrated lens micrometer and converting to millimeters (mm). Measurements were made blindly on precoded slides by two independent observers. The average of both observers' measurements were calculated, after which the code was broken and the data statistically analyzed. Each observer's measurements were generally within 5 percent of the other.

Histological analyses of the wounds immediately after wounding gave EG and GTG results of 538 and 24 (mean±SE, n=6), respectively, corresponding to expectations and thus validating the surgical wound method, the wound bisection technique, and the subsequent histological processing and analysis. The influx of new granulation tissue (NGT) was calculated on specific days postwounding by subtracting each GTG from the day zero GTG (5.38 mm). Approximate area and volume measurements for new granulation tissue were calculated, based on the assumption that the wounds healed concentrically and did not contract. The area of NGT was calculated by subtracting the remaining wound area on the day of harvest (calculated from the GTG) from the day zero wound area (22.7 mm$^2$). India ink tatoos were placed at the wound periphery on day zero to assess the degree of contraction during healing. After 7 days, wound diameters were unchanged. Infected wounds (less than 5%) or desicated wounds (less than 5%) were excluded before measurements were made. Cultures of clinically noninfected wounds were repeatedly conducted and showed no growth of pathogens.

Figure 8:
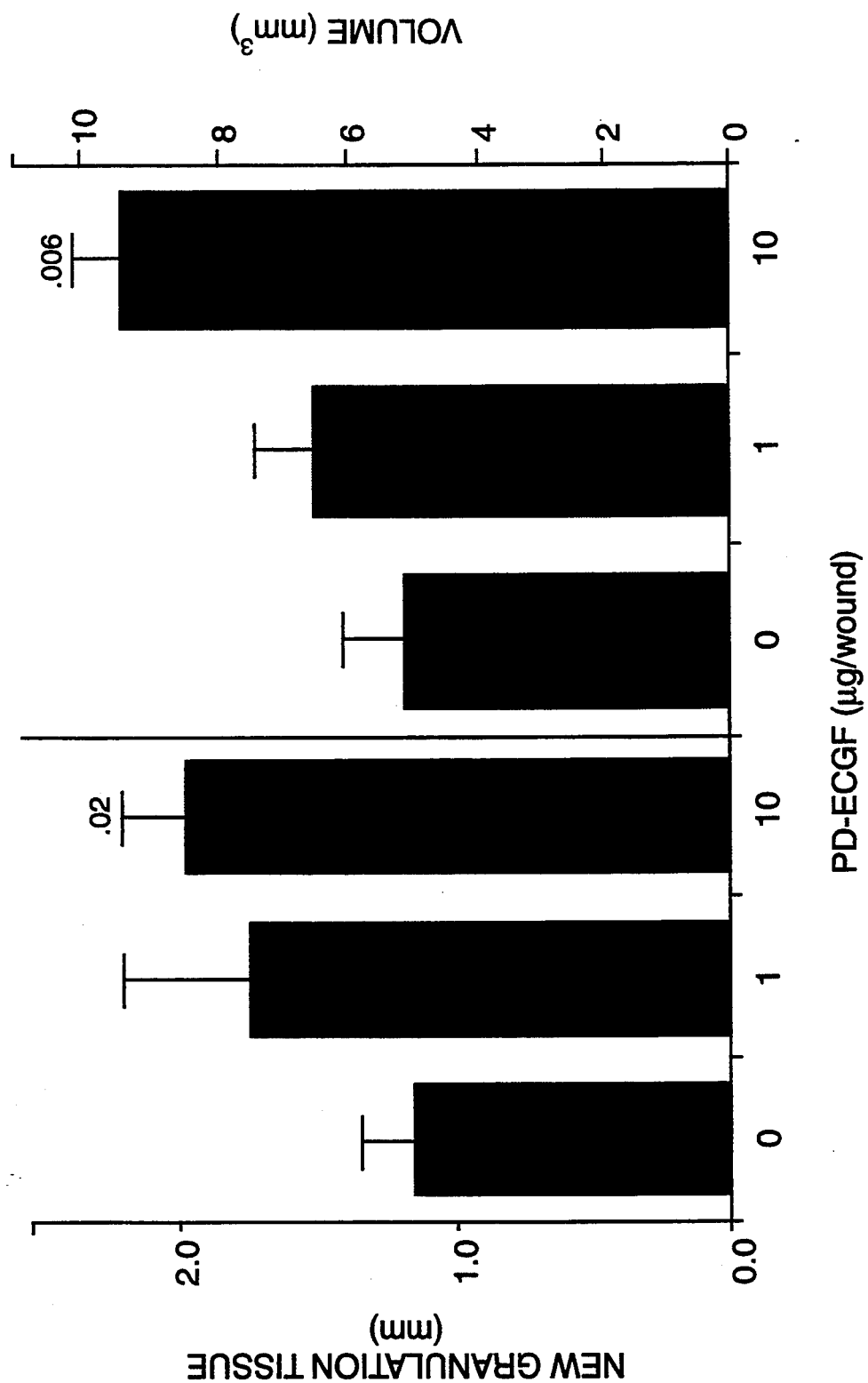
FIG. 8 shows the maximum height (MH) of granulation tissue at the advancing edges of the wound (light bars; units of mm) and approximate area and volume measurements for new granulation tissue were calculated (dark bars; units of mm$^3$), based on the assumption that the wounds healed concentrically and did not contract.

Nonparametric and parametric statistical analyses were carried out using SAS software. The resulting data are shown in Table 4. Similar experiments were performed using collagen wafer containing PDECGF. The resulting data for MH and the calculated volume of new granulation tissue is shown in FIG. 8.

TABLE 4

| The Effect of PDGF on Wound Healing with or Without Collagen as a Vehicle Material | | | | |
|---|---|---|---|---|
| | Control Buffer Solution | Control Collagen Wafer | PDGF-$\beta$ Buffer Solution | PDGF-$\beta$ Collagen Wafer |
| MH | 66.1 ± 8.74 | 74.3 ± 13.3 | 85.9 ± 9.5 | 86.6 ± 7.8 |
| GTG | 444 ± 51.75 | 450 ± 67.5 | 444 ± 48.2 | 410.1 ± 52.5 |
| New GTG | 124.7 ± 51.52 | 118.5 ± 67.9 | 122.6 ± 47.8 | 158.9 ± 60.4 |
| Area of New GT (mm$^2$) | 9.7 ± 3.62 | 9.2 ± 4.8 | 9.6 ± 3.4 | 12.0 ± 3.9 |
| EG | 87.1 ± 97.1 | 152.4 ± 154.5 | 143.5 ± 94.9 | 101.1 ± 140.7 |
| Vol of New GT (mm$^3$) | 6.5 ± 2.8 | 7.0 ± 4.3 | 8.1 ± 3.2 | 10.6 ± 4.2 |

Example 7: Measurement of Wound Healing in the Rabbit Stomach Stretch Model

The median gastric linear wound models were performed on an animal using a protocol approved by the institution's Animal Care and Use Committee. New Zealand White rabbits, 2.7 to 3.5 kg (Doe Valley Farms, Bentonville, Ark.) were preanesthetized by subcutaneous injection of atropine (0.1 mg/kg) and acepromazine (0.75 mg/kg). After a time span of 10 minutes, the animals were anesthetized with ketamine (0.75 mg/kg) and xylazine (5 mg/kg). Their abdomens were shaved with a #40 blade and sterilely prepared for surgery. A 10 cm midline laparotomy was made, the cecum was mobilized to expose the sacculus rotundus and approximately 20 cm of the cecum. Two haustra distal to the sacculus rotundus were counted off and paired 3 cm linear incisions were made parallel to the length of the cecum and 180 degrees opposite. Two more haustra were counted off the distal ends of the first two incisions and 2 or 3 cm incisions were made in like manner. To create a reproducible surgical plane, the incisions were carried through the serosal and muscular layers to leave the cecum mucosal layer intact. The collagen strips were then placed in the wound as to lay flat against the muscularis mucosae. The incisions were closed with a running 5-0 polypropylene suture (Ethicon Corp., Somerville, N.J.) at five sutures per centimeter and two millimeters from the wound margin. Sutures were placed through the serosal, muscular, and submuscular layers so as to draw these layers up and over the collagen strip against the muscularis mucosae. At the final knotting of the suture, the loop was trimmed in the control wounds and left intact in the experimental wounds so as to remove any chance of error at time of harvesting.

Care was taken to rotate the experimental therapy and the vehicle alone (control) between the four wounds. The laparotomy incision was closed by layers in the standard fashion. The animals were fed a standard diet (Tekland Rabbit Chow, Illinois) and given water ad libitum and housed individually in a controlled environment. On a predetermined day the animals were humanely euthanized with pentobarbitol (150 mg/kg) injected intravenously into the marginal ear vein. The wounded section of cecum was excised and the contents thoroughly flushed.

The suture was atraumatically removed from each wound and three standardized 8 mm strips were cut across each incision with the use of a punch template (Washington University machine shop). Histological samples were taken from areas between the wound strips. Wound breaking strength was measured in grams/mm$^2$ on a tensometer (Tensometer 10, Monsanto, St. Louis, Mo.) on three strips from each incision (six experimental, six control/rabbit). If evidence of infection, hematoma, or poor coaptation were evident, the sample was disregarded (<2% of all wounds were disregarded from analysis). All wounds were tested on the tesometer at 20 mm/min with the use of electrical claw clamps to insure breaking at the wound site only. Tensometry analysis was divided into three categories: fundal tissue, antral tissue, and cecal tissue and the data were reported individually for each.

Histological analysis was performed on matched samples from each group. Samples were sutured into microcasettes and stored in formalin and hemotoxlin and eosin staining was performed at a later date. The histological samples were then examined for thickness, amount of granulation tissue, and signs of necrosis, and these data were recorded.

Figure 9:
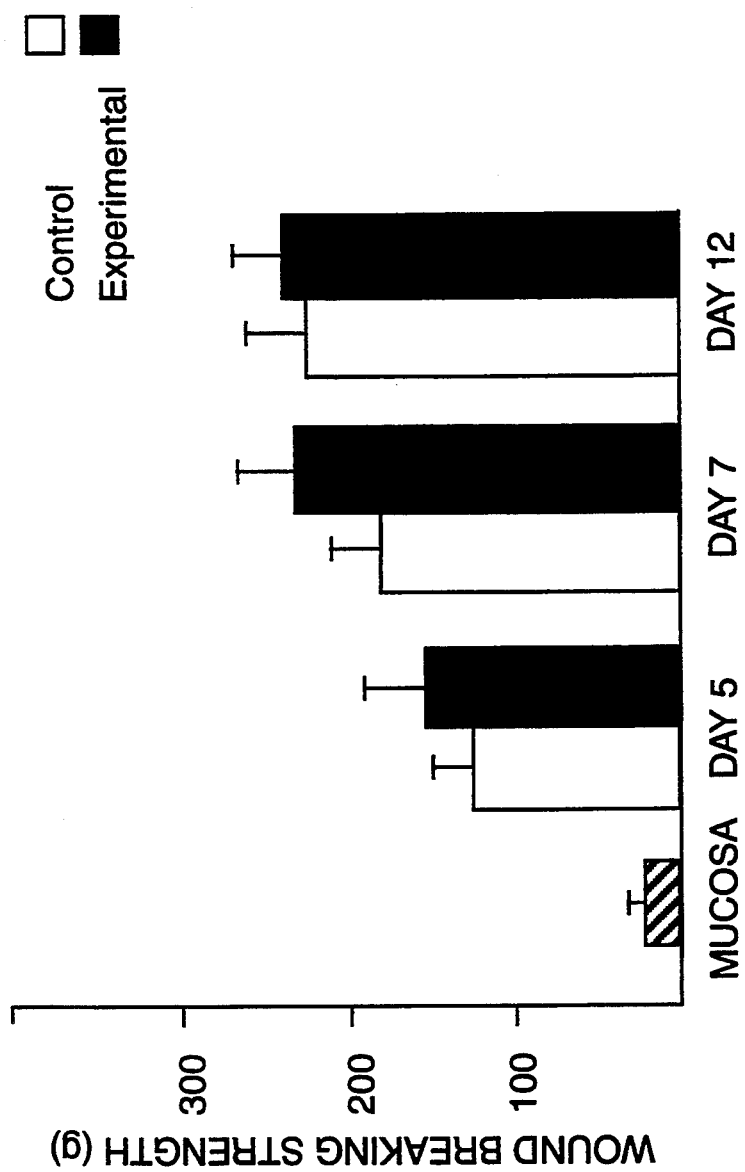
FIG. 9 shows effects of PDGF on the wound breaking strength when compared to untreated animals in the gastric linear wound model.

The results for secal tissue are shown in FIG. 9.

What is claimed is:

1. A multi-layered collagen film for use in controlled release of an active ingredient, said film comprising one or two rate controlling layers and one or more drug reservoir layers, said layers comprising non-fibrillar collagen and contacting each other in a stacked conformation such that a rate controlling layer is situated at one or both ends of the stack and contacts only one other layer, said other layer being a drug reservoir layer.

2. A collagen film according to claim 1 wherein one or both rate controlling layers further comprise an active ingredient.

3. A collagen film according to claim 1 wherein said rate controlling layers are devoid of any active ingredient.

4. A collagen film according to claim 3 wherein each of said drug reservoir layers further comprises an active ingredient.

5. A collagen film according to claim 4 wherein the number of said drug reservoir layers is from one to five.

6. A collagen film according to claim 5 wherein the number of said drug reservoir layers is from one to three.

7. A collagen film according to claim 6 wherein the number of said drug reservoir layers is three.

8. A collagen film according to claim 7 wherein one or both rate controlling layers and said drug reservoir layers each have a thickness of from about 0.01 mm to about 1 mm.

9. A collagen film according to claim 8 wherein one or both rate controlling layers and at least one of said drug reservoir layers each have a thickness of from about 0.05 to about 0.5 mm.

10. A collagen film according to claim 9 wherein one or both rate controlling layers and at least one of said drug reservoir layers each have a thickness of from about 0.1 mm to about 0.2 mm.

11. A collagen film according to claim 10 wherein one or both rate controlling layers further comprise a plasticizer.

12. A collagen film according to claim 11 wherein said one or more drug reservoir layers further comprise a plasticizer.

13. A collagen film according to claim 12 wherein one or both rate controlling layers further comprise a stabilizing agent.

14. A collagen film according to claim 13 wherein said one or more drug reservoir layers further comprise a stabilizing agent.

15. A collagen film according to claim 14 wherein one or both rate controlling layers further comprise a drying enhancer.

16. A collagen film according to claim 15 wherein said one or more drug reservoir layers further comprise a drying enhancer.

17. A collagen film according to claim 16 wherein one or both rate controlling layers further comprise a buffer.

18. A collagen film according to claim 17 wherein said one or more drug reservoir layers further comprise a buffer.

19. A collagen film according to claim 18 wherein said active ingredient is selected from the group consisting of PDGF, EGF, FGF, PDEGF, PD-ECGF, KGF, IGF-1, IGF-2, TNF, BDNF, CNTF, and NT-3.

20. A collagen film according to claim 19 wherein said active ingredient is PDGF.

21. A method of enhancing wound healing of an epidermal wound comprising administration of a wound healing effective amount of an active ingredient via a collagen film according to claim 1.

22. A collagen film according to claim 1, wherein a rate controlling layer is situated at both ends of the stack.

23. A collagen film according to claim 22 wherein said rate controlling layers further comprise an active ingredient.

24. A collagen film according to claim 22 wherein at least one of said rate controlling layers is devoid of any active ingredient.

25. A collagen film according to claim 24 wherein said drug reservoir layers further comprise an active ingredient.

26. A collagen film according to claim 25 wherein the number of said drug reservoir layers is from one to five.

27. A collagen film according to claim 26 wherein the number of said drug reservoir layers is from one to three.

28. A collagen film according to claim 27 wherein the number of said drug reservoir layers is three.

29. A collagen film according to claim 28 wherein said rate controlling layers and said drug reservoir layers each have a thickness of from about 0.01 mm to about 1 mm.

30. A collagen film according to claim 29 wherein one or both rate controlling layers and at least one of said drug reservoir layers each have a thickness of from about 0.05 to about 0.5 mm.

31. A collagen film according to claim 30 wherein one or both rate controlling layers and at least one of said drug reservoir layers each have a thickness of from about 0.1 mm to about 0.2 mm.

32. A collagen film according to claim 31 wherein at least one of said rate controlling layers further comprises a plasticizer.

33. A collagen film according to claim 32 wherein at least one of said drug reservoir layers further comprises a plasticizer.

34. A collagen film according to claim 33 wherein at least one of said rate controlling layers further comprises a stabilizing agent.

35. A collagen film according to claim 34 wherein at least one of said drug reservoir layers further comprises a stabilizing agent.

36. A collagen film according to claim 34 wherein at least one of said rate controlling layers further comprises a drying enhancer.

37. A collagen film according to claim 35 wherein at least one of said drug reservoir layers further comprises a drying enhancer.

38. A collagen film according to claim 36 wherein at least one of said rate controlling layers further comprises a buffer.

39. A collagen film according to claim 37 wherein at least one of said drug reservoir layers further comprises a buffer.

40. A collagen film according to claim 39 wherein said active ingredient is selected from the group consisting of PDGF, EGF, FGF, PDEGF, PD-ECGF, KGF, IGF-1, IGF-2, and TNF.

41. A collagen film according to claim 40 wherein said active ingredient is PDGF.

42. A method of enhancing wound healing of an internal wound comprising administration of a wound healing effective amount of an active ingredient via a collagen film according to claim 22.

43. A multi-layered collagen film for use in controlled release of an active ingredient, said film comprising at least two drug reservoir layers, said layers comprising non-fibrillar collagen and contacting each other in a stacked conformation.

44. A method of enhancing wound healing of an epidermal wound comprising administration of a wound healing effective amount of an active ingredient via a collagen film according to claim 43.

45. A method of enhancing wound healing of an internal wound comprising administration of a wound healing effective amount of an active ingredient via a collagen film according to claim 43.

* * * * *